(12) United States Patent
Misra et al.

(10) Patent No.: US 11,810,197 B2
(45) Date of Patent: Nov. 7, 2023

(54) SYSTEMS AND METHODS FOR BENEFIT PLAN QUALITY ASSURANCE AND CERTIFICATION

(71) Applicant: GalaxE.Solutions, Inc., Somerset, NJ (US)

(72) Inventors: Dheeraj Misra, Somerset, NJ (US); Sandipan Gangopadhyay, Somerset, NJ (US); Tim Bryan, Somerset, NJ (US)

(73) Assignee: GalaxE.Solutions, Inc., Somerset, NJ (US)

( * ) Notice: Subject to any disclaimer, the term of this patent is extended or adjusted under 35 U.S.C. 154(b) by 341 days.

(21) Appl. No.: 16/746,247

(22) Filed: Jan. 17, 2020

(65) Prior Publication Data
US 2020/0234381 A1    Jul. 23, 2020

Related U.S. Application Data

(60) Provisional application No. 62/794,367, filed on Jan. 18, 2019.

(51) Int. Cl.
| | |
|---|---|
| *G06Q 40/08* | (2012.01) |
| *G06F 3/04847* | (2022.01) |
| *G16H 10/60* | (2018.01) |
| *G06Q 10/1057* | (2023.01) |

(52) U.S. Cl.
CPC ......... *G06Q 40/08* (2013.01); *G06F 3/04847* (2013.01); *G06Q 10/1057* (2013.01); *G16H 10/60* (2018.01)

(58) Field of Classification Search
CPC .... G06Q 40/08; G06Q 10/1057; G16H 10/60; G06F 3/04847

USPC .......................................................... 705/2–3
See application file for complete search history.

(56) References Cited

U.S. PATENT DOCUMENTS

| | | | | |
|---|---|---|---|---|
| 5,950,169 | A * | 9/1999 | Borghesi ................ | G06Q 40/08 715/733 |
| 10,438,291 | B1 * | 10/2019 | Neben .................... | G06Q 40/08 |
| 2003/0149594 | A1 * | 8/2003 | Beazley ................ | G06Q 20/04 705/40 |

(Continued)

OTHER PUBLICATIONS

PCT/US20/14101, International Search Report (PCT/ISA/210 and PCT/ISA/220) dated Apr. 21, 2020, enclosing Written Opinion of the International Searching Authority (PCT/ISA/237) (Seven (7) pages).

(Continued)

*Primary Examiner* — Michael Tomaszewski
(74) *Attorney, Agent, or Firm* — Crowell & Moring LLP

(57) ABSTRACT

A system for testing a benefit plan for quality assurance is provided. A test adjudication engine is configured to process claims in accordance with the benefit plan, each of the claims having one or more parameters. A database is configured to store the benefit plan and quality assurance data, the quality assurance data including: (a) historical claims, each historical claim having an associated historical adjudication, and (b) new claims, each new claim not having an associated historical adjudication. An interactive dashboard is configured to allow a user to batch claims for processing by the test adjudication engine, from among the historical claims and the new claims, based on the one or more parameters.

18 Claims, 4 Drawing Sheets

(56) References Cited

U.S. PATENT DOCUMENTS

2011/0282690 A1* 11/2011 Patel .................. G16H 15/00
                                                                      705/3
2014/0081652 A1    3/2014 Klindworth

OTHER PUBLICATIONS

International Preliminary Report on Patentability (PCT/IB/326 and PCT/IB/373) and Written Opinion (PCT/ISA/237) dated Jul. 29, 2021 (Six (6) pages).
English-language Indian Office Action issued in Indian application No. 202117032252 dated Jan. 30, 2023 (Six (6) pages).

* cited by examiner

SYSTEMS AND METHODS FOR BENEFIT PLAN QUALITY ASSURANCE AND CERTIFICATION

CROSS-REFERENCE TO RELATED APPLICATIONS

This application claims the benefit of U.S. Provisional Application No. 62/794,367, filed on Jan. 18, 2019, the entire contents of which are hereby incorporated by reference.

BACKGROUND OF THE INVENTION

A typical benefit management enterprise manages hundreds if not thousands of individual benefit plans, including benefit plans for medical benefits and/or pharmaceutical benefits. These managed benefit plans typically include thousands of groups, millions of members, and hundreds of millions of claims to be processed.

The management of benefit plans also typically involves managing a combination of various disparate components, including data structures for the various aspects of the benefit plans, such as, for example, plan architecture, copays, formularies, networks, accumulators, etc. The intricate interdependencies between these components is usually not documented nor well understood due to the complex nature of the integrations among components.

In addition, in managing benefit plans, it is often necessary to track a large number of process steps as part of the benefit plan management, such as, for example, the process steps for adjudicating claims, including data inputs and data outputs at various steps of the process. Healthcare domains currently utilize either a combination of systems simplistic techniques, such as spreadsheets, emails, and handwritten notes, to capture and manage benefits. The use of such systems and techniques results in multiple challenges. These challenges include: higher costs of managing benefits, reliance on error prone manual work arounds, and a general lack of tracking and maintaining audit friendly information (which may be required for meeting compliance goals). As a consequence, data is often duplicated, and opportunities for the reuse of the benefits components are limited.

An additional consequence of traditional benefit management occurs when errors in adjudicating benefits claims within a claims processing IT environment manifest. Because of the lack of end-to-end traceability at each step of the adjudication processes, it is prohibitively difficult to determine the root cause of the error, as well as its potential effect on the adjudication of other claims. Moreover, if a root cause is eventually identified, it may not be readily foreseeable how changes to the benefit plan components addressing the root cause of the error might affect the adjudication of the changed benefit plan in other respects.

Similar consequences occur when new benefit plans, or changes to existing benefit plans, do not accurately reflect client intent. Because of the large number of components and general lack of end-to-end traceability, it is difficult to determine, once the benefit plan is implemented, the root cause of an inaccuracy, which makes it difficult to make the necessary corrections to align the benefit plan with the client intent.

Moreover, during quality assurance and certification testing of target benefit plans, as volumes of test claims increases, the risk of missing differences between test outcomes and intended outcomes also increases. These differences that can be critical to proper claim adjudication and detrimental to patient care.

In order to overcome the above challenges and to efficiently and effectively establish, change and/or otherwise manage benefit plans, the benefit management enterprise should be able to easily and quickly identify cross-dependencies among benefit plan components across the architectural tiers of the benefit plan. Moreover, the benefit plans managed, including new and changed benefit plans, should accurately reflect client intent.

Still further, the benefit plan management enterprise should be able to automate the quality assurance and certification testing related to target benefit plans when such testing involves adjudicating claim volumes that would be labor intensive and time-consuming to process manually. Accordingly, it should be easily and quickly verified that the target benefit plan was configured correctly, that it accurately reflects user intent, and that claims processed in accordance with the benefit plan are accurately adjudicated.

In that regard, a system and method for benefit plan management and certification, particularly in quality assurance and certification of target benefit plans having end-to-end traceability and built in accordance with captured user intent, is disclosed herein, which overcomes these and other shortcomings of prior systems and/or methods.

Other objects, advantages and novel features of the present invention will become apparent from the following detailed description of one or more preferred embodiments when considered in conjunction with the accompanying drawings. It should be recognized that the one or more examples in the disclosure are non-limiting examples and that the present invention is intended to encompass variations and equivalents of these examples. The disclosure is written for those skilled in the art. Although the disclosure use terminology and acronyms that may not be familiar to the layperson, those skilled in the art will be familiar with the terminology and acronyms used herein.

DETAILED DESCRIPTION OF EMBODIMENTS OF THE INVENTION

Figure 1:
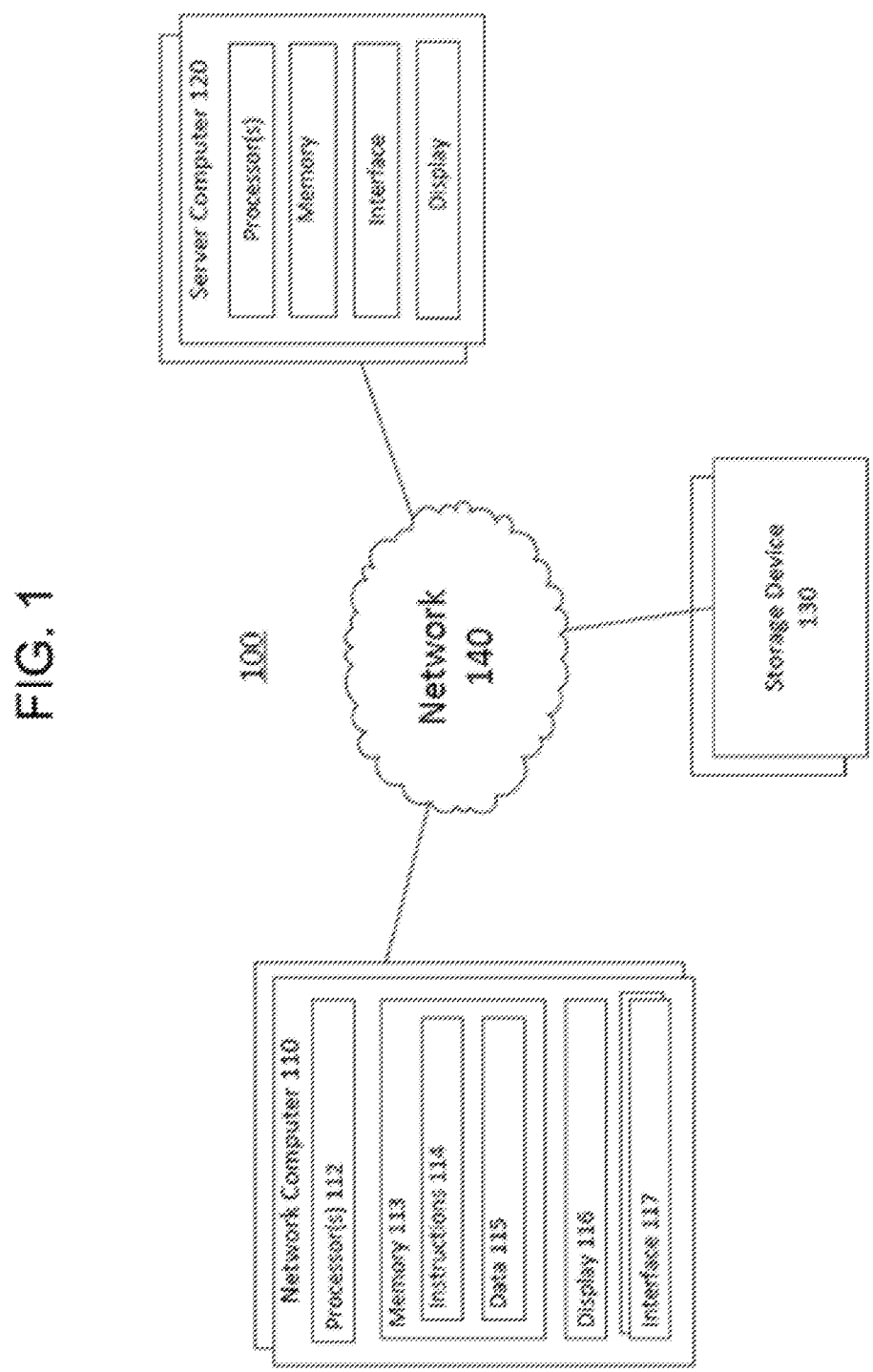
FIG. 1 illustrates an example system in accordance with one or more aspects of the disclosure.

The disclosure is directed to benefit plan management systems, and more particularly to more efficient management of benefit plans through the quality assurance and certification of such plans built in accordance with captured user intent and having end-to-end traceability.

A system and method for benefit plan certification is described herein. An interactive dashboard is utilized to accurately and automatically generate and assemble benefit components and associated rules for their implementation, which may be accordingly assembled to provide a target benefit plan in accordance with the intent of the user.

A benefit plan file is generated from the benefit components and associated rules according to the captured intent, which benefit file reflects the target benefit plan to be implemented on a target claims processing IT environment. The benefit plan file includes metadata associating benefit components with each other, as well as with and across benefit plan workflows, transitions, conditions, etc., which are also cross-referenced.

Accordingly, in at least one aspect, benefit plans in accordance with the intent of the user may be accurately and automatically built such that there is the ability to perform canonical and customized searches of dependent benefit components, workflows, transitions, conditions, etc., and generate impact reports that can show how desired changes to particular aspects may affect the adjudication of the benefit plan. To that end, manual identification of cross-dependencies and interpretation of data, for instance, may be eliminated.

The present disclosure provides a number of benefits and/or advantages over prior methods of enterprise benefits management. For example, the onboarding of new clients (i.e., employers, health care providers, etc.) to the benefit management system is facilitated by enabling accurate generation of benefit plans automatically in accordance with client intent, which benefit plans may be integrated with downstream benefits management systems, e.g., target claims processing IT environments.

Furthermore, inherent end-to-end traceability is available which may help eliminate the draw-backs of traditional benefits management systems, such as the failure to identify many critical components and dependencies, the duplication of such components, erroneous manual entries and work-arounds, and consistent documentation of the adjudication process. The reuse of benefit components instead of their unnecessary duplication may lead to lower maintenance costs due to a reduction in the number of benefit components that need to be maintained, leading to increased efficiencies in both build and maintenance.

An additional benefit and/or advantage, for example, may be an increased audit readiness, both for internal and external regulatory compliance, such as, for example, CMS directives, due to a reduction in the amount of time spent correlating information with a high degree of accuracy. The end-to-end traceability provided by the benefit plan file intrinsically provides such correlation, which in turn promotes efficiency and reduces errors during auditing.

A further benefit and/or advantage, for example, may be that end-to-end traceability may minimize or even eliminate unintentional impact to the claims adjudication process due to changes to the benefits plan. Impact assessment may drive and enhance the comprehensiveness of benefits plan requirements and design, and provide guidance for targeted regression analysis and test metrics, including an assessment of the risk associated with any proposed change to one or more components of the benefit plan. Test cases may be automatically generated and require only subject matter expert (SME) validation. Automation of quality assurance of claims processing may also be achieved by objectively determining criteria for selecting test claims based on the benefit changes made. Version tracking may likewise be improved.

A further benefit and/or advantage is the benefit plan quality assurance and certification testing of claim volumes that would be labor intensive and time-consuming to process manually. Moreover, narrow testing down to targeted content and demographics may be achieved, and testing utilizing both historical claims and new claims, e.g., for new products, may be accomplished. Certification may be further facilitated by establishing baseline test data with known historical outcomes. As such focus testing on changed aspects of the benefit plan, or on classes of outcomes that are relevant to such changed aspects, may be achieved. Accordingly, accurate verification that a target benefit plan was configured correctly and accurately reflects user intent may be improved.

A further benefit and/or advantage may be found in maximizing the effectiveness of quality analysts by organizing and classifying results into categories of differences to help quickly identify claims with similar/same differences. Moreover, tagging facilitates issue tracking, grouping and reporting of claims having the same issue. Workload may accordingly be reduced by avoiding rework/reanalysis after corrections and reruns.

As used herein, the terms "a" or "an" shall mean one or more than one. The term "plurality" shall mean two or more than two. The term "another" is defined as a second or more. The terms "including" and/or "having" are open ended (e.g., comprising). Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases in various places throughout this specification are not necessarily all referring to the same embodiment.

Furthermore, the particular features, structures, or characteristics may be combined in any suitable manner on one or more embodiments without limitation. The term "or" as used herein is to be interpreted as inclusive or meaning any one or any combination.

In accordance with the practices of persons skilled in the art, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the code segments to perform the necessary tasks. The code segments can be stored in a processor readable medium. Examples of the processor readable mediums include an electronic circuit, a semiconductor memory device, a read-only memory (ROM), a flash memory or other non-volatile memory, a floppy diskette, a CD-ROM, an optical disk, a hard disk, etc.

In the following detailed description and corresponding figures, numerous specific details are set forth in order to provide a thorough understanding of the present invention. However, it should be appreciated that the invention may be practiced without such specific details. Additionally, for brevity sake well-known methods, procedures, components, and circuits have not been described in detail.

FIG. 1 illustrates an example system 100 in accordance with one or more aspects of the disclosure. System 100 may include a plurality of computers and/or computing devices, such as, network computer 110, server computer 120, and storage device 130. By way of example only, network computer 110 is connected to network 140 and may include different types of components associated with a computer, such as one or more processors 112, memory 113, instructions 114, data 115, display 116, and an interface 117. The network computer 110 may be mobile (e.g., laptop computer, tablet computer, smartphone, PDA, etc.) or stationary (e.g., desktop computer, etc.). Similarly, server computer 120 may also include one or more processors, memory, interface, and/or display and may be configured to communicate with other computer devices on network 140.

The processor 112 of network computer 110 may instruct the components thereof to perform various tasks based on the processing of information and/or data that may have been previously stored or have been received, such as instructions 114 and/or data 115 stored in memory 113. The processor 112 may be a standard processor, such as a central processing unit (CPU), or may be a dedicated processor, such as an application-specific integrated circuit (ASIC) or a field programmable gate array (FPGA).

Memory 113 stores at least instructions 114 and/or data 115 that can be accessed by processor 112. For example, memory 113 may be hardware capable of storing information accessible by the processor, such as a ROM, RAM, hard-drive, CD-ROM, DVD, write-capable, read-only, etc. The set of instructions may be included in software that can be implemented on the network computer 110 and should be noted that the terms "instructions," "steps," "algorithm," and "programs" may be used interchangeably. Data 115 can be retrieved, manipulated or stored by the processor 112 in accordance with the set of instructions 114 or other sets of executable instructions. The data 115 may be stored as a collection of data.

The display 116 may be any type of device capable of communicating data to a user, such as a liquid-crystal display ("LCD") screen, a plasma screen, etc. Interface 117 allow a user to communicate with the network computer 110 and may be a physical device (e.g., a port, a keyboard, a mouse, a touch-sensitive screen, microphone, camera, a universal serial bus (USB), CD/DVD drive, zip drive, card reader, etc.) and/or may be virtual (e.g., a graphical user interface "GUI," etc.).

The server computer 120 (and additional server computers) may be rack mounted on a network equipment rack and/or located, for instance, in a data center. In one example, the server computer 120 may use the network 140 to serve the requests of programs executed on network computer 110 and/or storage device 130.

The storage device 130 illustrated in FIG. 1 may be configured to store large quantities of data and/or information. For example, the storage device 130 may be a collection of storage components, or a mixed collection of storage components, such as ROM, RAM, hard-drives, solid-state drives, removable drives, network storage, virtual memory, cache, registers, etc. The storage device 130 may also be configured so that the network computer 110 and/or server computer 120 may access it via the network 140.

The network 140 may be any type of network, wired or wireless, configured to facilitate the communication and transmission of data, instructions, etc. from one component to another component of the network. For example, the network 140 may be a local area network (LAN) (e.g., Ethernet or other IEEE 802.03 LAN technologies), Wi-Fi (e.g., IEEE 802.11 standards, wide area network (WAN), virtual private network (VPN), global area network (GAN)), any combination thereof, or any other type of network.

It is to be understood that the network configuration illustrated in FIG. 1 serves only as an example and is thus not limited thereto. System 100, for instance, may include numerous other components connected to network 140, include more than one of each network component (as shown by the cascaded blocks), and network 140 may be connected to other networks.

Figure 2:
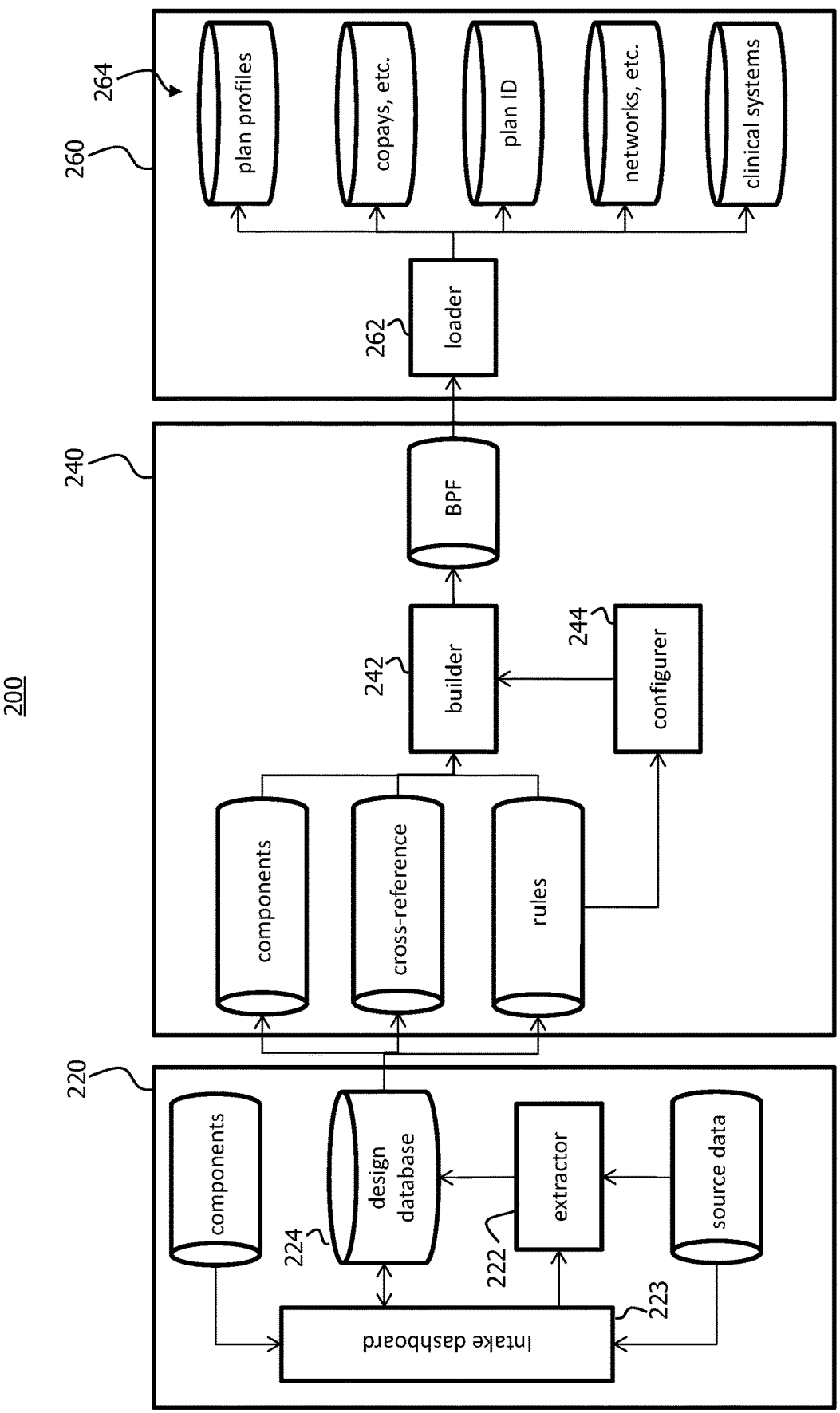
FIG. 2 illustrates a diagram of the architecture in accordance with one or more aspects of the disclosure.
Figure 3:
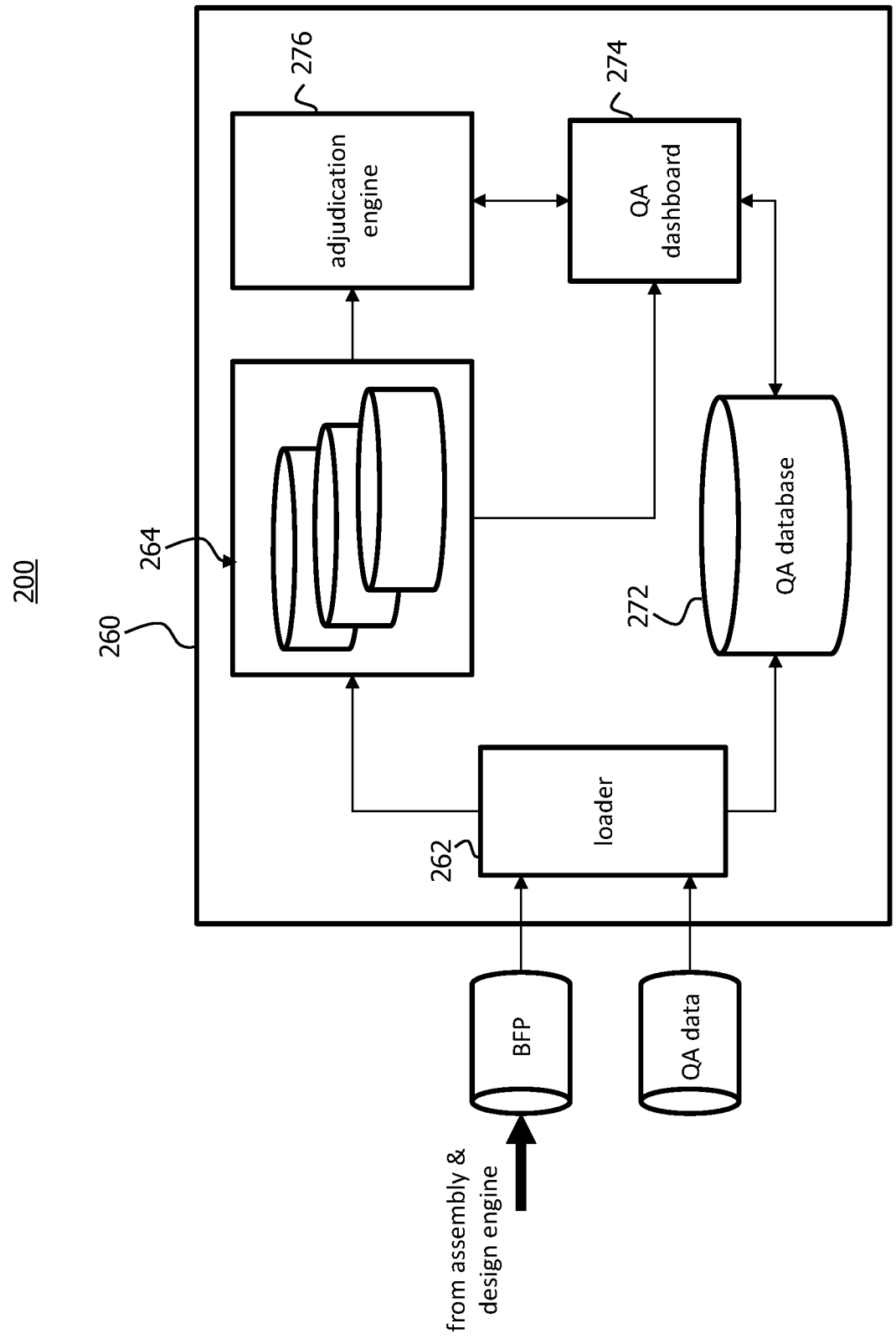
FIG. 3 illustrates a diagram of the architecture in accordance with one or more aspects of the disclosure

FIGS. 2 and 3 illustrate one embodiment of an exemplary architecture 200 for benefit plan management and certification. The architecture 200, as shown in FIG. 2, includes an intake engine 220, an assembly and design engine 240, and a target claims processing IT environment 260. The intake module 220 includes an extractor 222, an intake dashboard 223, and a design database 224. The assembly and design module 240 includes a builder 242 and a configurer 244. The target claims processing IT environment 260 includes a loader 262 and one or more environment databases 264. FIG. 3, shows the target claims processing IT environment 260 configured for benefit plan certification. As shown in FIG. 3, the target claims processing IT environment further includes a quality assurance database 272, a quality assurance dashboard 274, and an adjudication engine 276.

One example of the operation of the system architecture shown in FIGS. 2 and 3 is as follows. In operation, the system may generate claims, in for example D.0 format, and submit the claims to an adjudication system, e.g., the target claims processing IT environment, for processing in accordance with the benefit plan.

User intent with respect to the design and configuration of the target benefit plan is determined via the intake module 220, which may be configured to intake source data, as well as benefit components and associated rules utilized in assembling the target benefit plan. The intake dashboard 223 may provide functions enabling the intake module 220 to intake such information, and to determine the user intent. As such, the intake dashboard 223 may be accessible to the user via the GUI through a real-time interactive web portal.

Intake source data reflecting a source benefit plan (i.e., benefit plan data) may be provided to the extractor 222, either directly or via the intake dashboard 223, which extractor 222 may utilize automated parsing and cross-application dependency mapping techniques to identify different benefit components within the source benefit plan and their cross-dependencies, which extracted information is populated into the design database 224. The intake source data may be formatted according to various formats, such as, for example, XML, Excel, Claims System, and Requirements Doc. formats. The intake source data may be provided from a source system, such as, for example, source systems of employer groups and/or internal product design groups. Exemplary automated parsing and cross-application dependency mapping techniques that may be utilized are disclosed, for example, in U.S. application Ser. No. 15/087,786, entitled "System and method for Automated Cross-Application Dependency Mapping," filed on Mar. 31, 2016, the contents of which are incorporated herein by reference in its entirety.

The benefit components populated into the design database 224 include data structures reflecting various aspects of the source benefit plan. For example, benefit components may include plan copays, formularies, networks, accumulators, etc., as well as associated rules for their implementation with respect to the source benefit plan, e.g., workflow call mapping and configuration. The benefit components and their cross-dependencies may also be provided directly to the design database 224 via the intake dashboard 223.

Using the dashboard 223, the user defines and maps the target benefit plan hierarchy, which definitions and mapping are populated to the design database 224. The target benefit plan hierarchy may be defined and mapped through the manual selection and/or entry of benefit plan components. In addition or alternatively thereto, the dashboard 223 may provide a preliminarily defined and mapped target benefit plan, which may be generated based on the intake source data, such as, for example, the intake source data of an template benefit plan.

After the target benefit plan hierarchy is defined and mapped, the dashboard 223 provides to the user one or more questionnaires that are configured to further elicit user intent. Machine learning artificial intelligence may be utilized to design the questionnaire based on the information populated into the design database. The design of the questionnaire may include configurations for tabs or pages, page groups, questions and answers.

User responses to the questionnaires are utilized to configure rules according to which the target benefit plan is to be built, which rules are populated to the design database 224. These rules, for example, may indicate pharmaceutical drug dispensing conditions and/or limitations, etc. The rules are configured by configuring rule categories and loading pre-configured rules and actions. Rules categories may, for example, include: dataset, scenario, templates, record rules, and field rules. Dataset rules may refer to component definitions, such as, for example, Plan, Patient, Pay/Copay, Accumulations, etc. Scenario rules may refer to conditions under which components are called, such as, for example, under Flat Copay or Stepped Copay conditions. Templates rules may refer to definitions for sub-components to be built within the dataset, such as, for example, Patient Pay Schedules with Min/Max, and Patient Pay Schedules without Min/Max. Record rules may refer rules to get data from input. Field rules may refer to rules defined for each field. Machine learning artificial intelligence may be utilized to configure the rules based on the information populated into the design database.

The configured rules are then utilized to configure workflows in accordance with the target benefit plan, which workflows are populated to the design database 224. These workflows, for example, may indicate processing procedures for adjudicating benefits claims, etc. The workflows are configured by configuring activities and steps for the various workflows, workflow transitions and conditions, and workflow roles. Machine learning artificial intelligence may be utilized to configure the workflows based on the information populated into the design database.

The determined user intent with respect to the design and configuration of the target benefit plan, including benefit components and associated rules utilized in assembling the target benefit plan may be exported and assembled into a target benefit plan file in accordance therewith. In this manner, custom target benefit plans having end-to-end traceability, including traceability among and across business, technical and system setup requirements, may be accurately and automatically designed and assembled.

The benefit components populated into the design database 224 are then assembled into a target benefit plan file by the builder 242 in accordance with the various benefit components and associated rules, the benefit plan file reflecting the target benefit plan. The benefit plan file includes data structures and metadata associating benefit components with each other, as well as with and across benefit plan workflows, transitions, conditions, etc., which are also cross-referenced.

In assembling the target benefit plan file, the builder 242 utilizes cross-references between benefit components, in order to avoid the use of duplicative components in building the benefit plan file, and to reuse components for different aspects of the target benefit plan represented by the benefit plan file. To that end, the builder 242 may also create model benefit components from the information in the design database 224, the model benefit components supplanting one or more benefit components.

The builder 242 also utilizes associated mapping rules to configure the benefit components according to the configuration of the target benefit plan. The benefit plan file configuration is provided by a configurer 244, which generates the target benefit plan file configuration from the mapping rules, and provides the benefit plan file configuration to the builder 242. The benefit plan file configuration associates the various benefit components to the target benefit plan workflows, transitions, conditions, etc.

The builder 242 is also provided with a layout reflecting the layout necessary for the target benefit plan file to be successfully loaded into a target claims processing IT environment 260. The builder 242 utilizes the layout to translate the target benefit plan into the benefit plan file having the appropriate layout.

The loader 262 loads the appropriate data from the benefit plan file into relevant associated databases 264 of the target claims processing IT environment 260, which may include databases for plans and plan profiles; copays, drug lists, coverages, DURs, and formularies; client plan ID cross-references; networks and accumulators; and clinical systems. It will be understood, however, that the loading is in accordance with the layout of the target claims processing IT environment 260.

In some embodiments, the target claims processing IT environment 260 is a virtual staging environment via which user interaction with the target benefit plan is possible. The target benefit plan may be accessed by the user through the input/output device, such as a GUI of the network computer 110 and/or the server computer 120, as illustrated in FIG. 1, via a dashboard (not shown). By way of example, interaction with the target benefit plan may include business level review of the benefit plan, testing, editing, generation of summaries, change reports and lists of benefit components. For instance, the target benefit plan may be used to generate service reports for particular end users, customers, and/or consumers, which may be a series of reports on the various aspects of the target benefit plan. These service reports may provide detailed analysis of the various aspects, e.g., components, and their overall impact and/or implications on the target benefit plan. In one example, a service report may be in digital format and may be utilized on one or more GUIs by the end user, customers, and/or consumers.

Turning now to FIG. 3, in accordance with further aspects, the target claims processing IT environment 260 automatically tests benefit claims related to the loaded target benefit plan so as to facilitate quality assurance and certification for claim volumes that would be labor intensive and time-consuming to process manually. The target claims processing IT environment 260 further verifies that the target benefit plan is configured without error and that the target benefit plan accurately reflects the captured user intent. The verification, through automated quality assurance and certification testing, verifies that claims processed in accordance with the target benefit plan are accurately adjudicated in accordance with the captured intent.

Quality assurance related data is uploaded via the loader 262 and populated into the quality assurance database 272. The quality assurance related data may additionally or alternatively be manually entered and populated into quality assurance database. The quality assurance related data may include, for example, historical claims, new claims, benefit eligibility group lists, and other quality assurance related data usable to conduct quality assurance and certification testing of benefit plans.

The quality assurance dashboard 274 is then utilized to define the scope of a test adjudication. Accordingly, the quality assurance dashboard 274 may comprise a dashboard engine operatively coupled to the interface 117, e.g., GUI, so as to permit user interaction with target claims processing environment 260 in accordance with the functionalities disclosed herein.

In defining the scope of the test adjudication, the quality assurance dashboard 274 may access the associated databases 264 and retrieve benefit plan related data, e.g., definitions, scenarios, hierarchy map, etc., as well as the quality assurance database 272, for the information populated therein. For example, the user may define the scope of the test adjudication by selecting batches of new and/or historical claims. Historical claims may be selected by scenarios, which filter the historical claims. Such scenarios may consider factors such as, for example, date ranges, PNC, random drugs, formularies, group lists, member lists, members having large numbers of claims, prior authorizations, gender, age, drug tier, drug multisource code, in or out of network, and claims for specific plans, providers, prescribers, copay schedules/rule sets, prescriptions, networks, deductible schedules/rulesets, out of pocket schedule/rule set, etc. Selected historical scenarios may be augmented with randomly selected claims and/or specifically identified new claims. The selected batches of claims are then provided to the adjudication engine 276 for test adjudication.

The adjudication engine 276 then processes the selected batches of claims in accordance with the target benefit file. As such, the adjudication engine is configured to access the various aspects of the benefit plan file loaded on the target claims processing IT environment 260 via the associated databases 264. The selected batches of claims are processed with reference to relevant aspects of the benefit plan, and the claims are accordingly adjudicated in accordance with the target benefit plan.

The outcomes of the adjudication are provided to the quality assurance dashboard 274. The quality assurance dashboard is further configured to compare the outcomes of the test adjudication to historical outcomes for the selected batches. The quality assurance dashboard 274 may also be configured to determine baselines from the historical outcomes, and to compare the test adjudication outcomes to the determined baselines. The quality assurance dashboard 274 may further be configured to apply user-defined thresholds to filter out expected differences.

The quality assurance dashboard 274 may also be configured to categorize differences and generate summaries for presentation and drill down analysis. Such categorizing may involve utilizing pattern matching. Reports may be generated, as described herein, which include the test adjudication outcomes, and which may also include the historical outcomes in side-by-side comparison.

Reported results can be reviewed by subject matter experts and business level users to determine errors in the target benefit plan to be corrected. Corrections to the target benefit plan, for example, via the assembly and design engine 240, may thus be made. Reprocessing and reanalyzing the batches may also occur after any such corrections are made.

The quality assurance dashboard may also enable tagging and exporting claims for root cause analysis, and/or tagging claims as defining acceptable/expected differences. Such tagged claims may be saved within the QA database for further reference during reprocessing and/or reanalyzing of the batches. Accordingly tagging may be pulled forward from previous results.

The quality assurance dashboard may further be configured to allow a user to visually expand the batched claims into a list of its component claims, and to select individual claims (and associated adjudications) for juxtaposition between, for example, the adjudication of the selected claim and historical adjudications (or baselines). The juxtaposition may be a field-by-field (i.e., parameter by parameter) juxtaposition. Where a new claim is selected, for which there is no historical adjudication, the juxtaposition may be with the baseline or with a similar historical claim.

Figure 4:
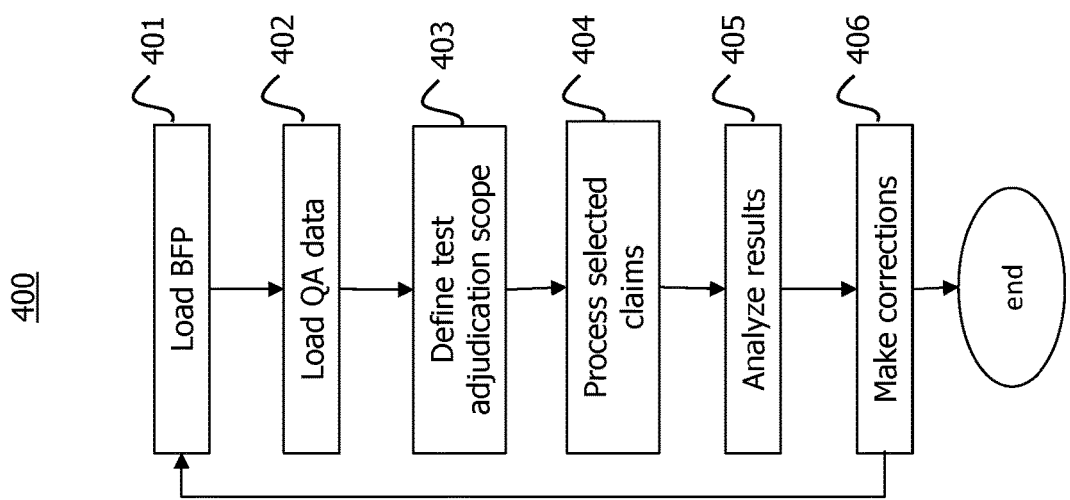
FIG. 4 illustrates a flow diagram of an algorithm used by the architecture in accordance with one or more aspects of the disclosure.

As described above, FIG. 4 illustrates a flow-diagram 400 of an algorithm used by the architecture of FIG. 3 in accordance with one or more aspects of the disclosure.

At step 401, the benefit plan file is loaded, via the loader 262, into the target claims processing IT environment 260, including associated databases 264. At step 402, quality assurance related data, including claims, is uploaded (if it is not already uploaded), via the loader 262, and populated into the quality assurance database 272.

At step 403, the scope of the test adjudication is defined, via the quality assurance dashboard 274, by selecting batches of claims to be test adjudicated. At step 404, the selected batches of claims are processed by the adjudication engine 276 in accordance with the target benefit file. At step 405, the outcomes of the test adjudication are compared to historical outcomes (i.e., historical adjudication or a baseline generated therefrom) for the selected batches of claims, and reports summarizing the results are generated and presented. The summarized reports may categorize the types of mismatches or differences found between the baseline or historical adjudication and the test adjudication.

At step 406, corrections to the target benefit plan, for example, via the assembly and design engine 240, are made. The quality assurance and certification process may then be repeated by returning to step 301.

In accordance with foregoing embodiments, examples, and/or aspects of the invention, all dependencies between benefit components within the target benefit plan are identified. For any benefit component, it is possible to identify all relevant callers across the target benefit plan at any point in time. End-to-end traceability of benefit components across the target benefit plan is therefore provided. A trace may be viewed by starting at any level of the target benefit plan, and the source component that invokes the relevant function, transaction, service, or aspect of the target benefit plan may be identified. The embodiments of the invention therefore provide the ability to search all callers of a particular component across the target benefit plan. In addition, potential orphans and duplicates can be identified.

In a further aspect of the disclosure, as discussed herein, an easy-to-use, intuitive GUI is provided that includes the dashboard that permits a user to view end-to-end traceability of relevant benefit components, functions, transactions, services, or aspects, and to view and navigate between architectural tiers of the target benefit plan (e.g., business processes, workflows and rules, use and/or test cases, component definitions, data elements, etc.). Links may be provided within the GUI that can be clicked by a user in order to navigate directly to the relevant component from a given use case, test case, or business rule, and vice versa.

In a further aspect of the disclosure, end-to-end traceability and benefit claim design and configuration is integrated with claims processing quality assurance analysis, facilitating end-to-end audits of target benefit plans from intake through certification.

While certain exemplary embodiments have been described and shown in the accompanying drawings, it is to be understood that such embodiments are merely illustrative of and not restrictive on the broad inventions, and that this inventions not be limited to the specific constructions and arrangements shown and described, since various other modifications may occur to those ordinarily skilled in the art.

The invention claimed is:

1. A system for building and testing a target benefit plan file, the system comprising:
   an intake engine configured to intake source files reflecting a source benefit plan and to apply automated parsing and cross-application dependency mapping to identify a plurality of benefit plan components and associated cross-dependencies from the source files, wherein the automated parsing and cross-application dependency mapping includes:
     placing file paths of the source files into a parsing queue,
     starting a plurality of configured threads,
     selecting, by each configured thread, a respective source file corresponding to a file path stored in the parsing queue,
     looping, by each respective configured thread, through each respective line in the associated selected source file associated with the respective configured thread, in order to obtain parsed information characterizing execution dependencies for function, transaction and service calls of each of the benefit plan components with and across administrative workflows and systems;
   a build engine configured to autonomously generate model benefit plan components from duplicative benefit plan components in the plurality of benefit plan components, and to assemble the target benefit plan file from the model benefit plan components, wherein the target benefit plan file is a compiled computer data object that maps the identified cross-dependencies of the benefit plan components based on the parsed information;
   a test adjudication engine operating within a virtual staging environment, configured to execute a test adjudication that test processes claims in accordance with the target benefit plan file being tested so as to determine whether the target benefit plan file is built in accordance with a captured user intent, each of the claims having one or more parameters;
   a database, configured to store the benefit plan file and quality assurance data, the quality assurance data including: (a) historical claims, each historical claim having an associated historical adjudication, and (b) new claims, each new claim not having an associated historical adjudication; and
   a graphical user interface, including an interactive dashboard configured to:
     allow a user to interact with the virtual staging environment so as to define a scope of the test adjudication by selectively batching claims for the test adjudication processing by the test adjudication engine, from among the historical claims and the new claims, based on the one or more parameters; and
     allow the user to visually navigate, via one or more hyperlinks, between and within architectural tiers of the target benefit plan file being tested, so as to trace the test adjudication between the architectural tiers of the target benefit plan file being tested.

2. The system of claim 1, wherein the parameters include: claim dates, medications claimed, associated drug tier/code, and/or medical procedures claimed.

3. The system of claim 1, wherein the parameters include claimant parameters, including: claimant gender, claimant age, claimant medical conditions, and/or number of other claims made by claimant.

4. The system of claim 1, wherein the parameters include associated plan parameters, including: PNC status, associated formularies, associated group lists, associated member lists, prior authorizations, in-network or out-of-network, associated plans, associated providers, associated prescribers, associated copay schedules/rule sets, associated prescription networks, deductible schedules/rule sets, and/or out-of-pocket schedules/rule sets.

5. The system of claim 1, wherein the interactive dashboard is configured to allow the user to randomly batch claims for processing by the text adjudication engine.

6. The system of claim 1, wherein the interactive dashboard is configured to present a comparison of the adjudicated batched claims to the historical adjudications.

7. The system of claim 1, wherein the interactive dashboard is configured to filter out expected differences between the adjudicated batched claims and the historical adjudications.

8. The system of claim 1, wherein the interactive dashboard is configured to compare the adjudicated batched claims to one or more baselines derived from the historical adjudications.

9. The system of claim 1, wherein the interactive dashboard is configured to tag claims as defining acceptable or expected differences.

10. A method for building and testing a target benefit plan file, the method comprising:
    intaking source files reflecting a source benefit plan;
    applying automated parsing and cross-application dependency mapping to identify a plurality of benefit plan components and associated cross-dependencies from the source files, wherein the automated parsing and cross-application dependency mapping includes:
      placing file paths of the source files into a parsing queue,
      starting a plurality of configured threads,
      selecting, by each configured thread, a respective source file corresponding to a file path stored in the parsing queue,
      looping, by each respective configured thread, through each respective line in the associated selected source file associated with the respective configured thread, in order to obtain parsed information characterizing execution dependencies for function, transaction and service calls of each of the benefit plan components with and across administrative workflows and systems;
    autonomously generating model benefit plan components from duplicative benefit plan components in the plurality of benefit plan components;
    assembling the target benefit plan file from the model benefit plan components, wherein the target benefit plan file is a compiled computer data object that maps the identified cross-dependencies of the benefit plan components based on the parsed information;
    storing, in a database, the target benefit plan file and quality assurance data, the quality assurance data including: (a) historical claims, each historical claim having an associated historical adjudication, and (b) new claims, each new claim not having an associated historical adjudication, defining a scope of a test adjudication by selectively batching, via an interactive dashboard of a graphical user interface, claims for the test adjudication to be processed by a test adjudication engine, from among the historical claims and the new claims, based on one or more parameters;

test processing the claims, via the test adjudication engine operating within a virtual staging environment, in the course of the test adjudication, in accordance with the target benefit plan file being tested so as to determine whether the target benefit plan file is built in accordance with a captured user intent; and providing one or more hyperlinks to the interactive dashboard, via which the user may visually navigate between and within architectural tiers of the target benefit plan file being tested, so as to trace the test adjudication between the architectural tiers of the target benefit plan file being tested.

11. The method of claim 10, wherein the parameters include: claim dates, medications claimed, associated drug tier/code, and/or medical procedures claimed.

12. The method of claim 10, wherein the parameters include claimant parameters, including: claimant gender, claimant age, claimant medical conditions, and/or number of other claims made by claimant.

13. The method of claim 10, wherein the parameters include associated plan parameters, including: PNC status, associated formularies, associated group lists, associated member lists, prior authorizations, in-network or out-of-network, associated plans, associated providers, associated prescribers, associated copay schedules/rule sets, associated prescription networks, deductible schedules/rule sets, and/or out-of-pocket schedules/rule sets.

14. The method of claim 10, wherein the interactive dashboard is configured to allow the user to randomly batch claims for processing by the text adjudication engine.

15. The method of claim 10, wherein the interactive dashboard is configured to present a comparison of the adjudicated batched claims to the historical adjudications.

16. The method of claim 10, wherein the interactive dashboard is configured to filter out expected differences between the adjudicated batched claims and the historical adjudications.

17. The method of claim 10, wherein the interactive dashboard is configured to compare the adjudicated batched claims to one or more baselines derived from the historical adjudications.

18. The method of claim 10, wherein the interactive dashboard is configured to tag claims as defining acceptable or expected differences.

* * * * *